US005892143A

United States Patent [19]
Namerikawa et al.

[11] Patent Number: 5,892,143
[45] Date of Patent: Apr. 6, 1999

[54] SENSOR DEVICE WITH FLUID INTRODUCTION HOLES

[75] Inventors: Masahiko Namerikawa, Kounomiya inazawa; Kazuyoshi Shibata, Nagoya; Yukihisa Takeuchi, Nishikamo-gun, all of Japan

[73] Assignee: NGK Insulators, Ltd., Japan

[21] Appl. No.: 857,338

[22] Filed: May 16, 1997

[30] Foreign Application Priority Data

May 22, 1996 [JP] Japan ..................................... 8-127278
Jun. 21, 1996 [JP] Japan ..................................... 8-162187

[51] Int. Cl.⁶ ............................. G01L 1/16; G01N 11/10
[52] U.S. Cl. ...................... 73/54.24; 73/54.27; 73/54.41; 310/324; 310/338
[58] Field of Search ............................. 73/54.24, 54.27, 73/54.41, 54.01; 310/324, 338

[56] References Cited

U.S. PATENT DOCUMENTS

| 4,721,874 | 1/1988  | Emmert .       |         |
| 4,741,200 | 5/1988  | Hammerle .     |         |
| 4,961,345 | 10/1990 | Tsuruoka et al. . |      |
| 5,334,303 | 8/1994  | Muramatsu et al. . |     |
| 5,374,521 | 12/1994 | Kipling et al. . |       |
| 5,485,744 | 1/1996  | Akutagawa et al. . |     |
| 5,545,461 | 8/1996  | Takeuchi et al. ........................ | 428/138 |
| 5,600,197 | 2/1997  | Takeuchi et al. .................... | 310/324 X |
| 5,698,931 | 12/1997 | Shibata et al. ...................... | 73/54.27 X |

FOREIGN PATENT DOCUMENTS

| 0226570 | 6/1987 | European Pat. Off. . |         |
| 0714022 | 5/1996 | European Pat. Off. .............. | 73/54.24 |
| 1-311250 | 12/1989 | Japan . |
| 2-213743 | 8/1990  | Japan . |
| 3-148040 | 6/1991  | Japan . |

OTHER PUBLICATIONS

Patent Abstracts of Japan, vol. 006, No. 008 (P–098), Jan. 1982.

Electrochemical Acta, vol. 41, No. 10, Jun. 1996, pp. 1721–1726, "Determination of the State–of–Charge of a Lead–Acid Battery Using Impedance of the Quartz Crystal Oscillator", by John M. Charlesworth.

Primary Examiner—Daniel S. Larkin
Attorney, Agent, or Firm—Parkhurst & Wendel, L.L.P.

[57] ABSTRACT

A sensor device includes a base body 12 having a vibrating portion 14, a piezoelectric element 20 fixed onto one surface of the vibrating portion 14 and having a piezoelectric film 22 and a pair of electrodes 24a, 24b which are in contact with the piezoelectric film 22, a space 16 that allows a fluid to lead to the other surface of the vibrating portion 14, and introduction holes 18 that communicate with the space 16, and the sensor device 10 is in a longitudinal shape. A recess 15 which contains at least an opening end of the introduction hole 18 on the surface side of the sensor device 10 in its region and extends up to the rear end portion 10' of the sensor device is formed on the surface of the sensor device 10 by a protrusion 13 disposed on the surface of said sensor device so as to extend substantially continuously from the periphery of the introduction holes 18 to the rear end portion 10' of said sensor device.

2 Claims, 20 Drawing Sheets

SENSOR DEVICE WITH FLUID INTRODUCTION HOLES

BACKGROUND OF THE INVENTION AND RELATED ART STATEMENT

The present invention relates to a sensor device having a piezoelectric element for measuring the viscosity, the density, the concentration, etc., of a fluid.

Up to now, in order to measure the viscosity, the density, the concentration, etc., of a fluid, a sensor device using a vibrator such as a piezoelectric element has been used. FIGS. 20A and 20B show an example of the sensor device of this type, in which FIG. 20A is a perspective view of the sensor device, and FIG. 20B is a partially enlarged cross-sectional view of the sensor device taken along a line VI—VI. The sensor device 40 includes a base body 12 having a thin vibrating portion 14. Onto one surface of the vibrating portion 14 is fixed a piezoelectric element 20 having a piezoelectric film 22 and a pair of electrodes 24a and 24b which are disposed to be in contact with the piezoelectric film 22, and the other surface of the vibrating portion 14 faces a space (surrounded space) 16 defined in the interior of the base body.

Also, introduction holes 18 that communicate with the space 16 are defined in the vicinity of a tip of the sensor device 40 in such a manner that a fluid flowing into the space 16 from the introduction holes 18 is led to the vibrating portion 14. The piezoelectric element 20 is covered with a protective cover 17 so as not to be in direct contact with the fluid.

In the sensor device 40 thus structured, a fluid to be measured is allowed to flow into the space 16 from the introduction holes 18 so as to be in contact with the vibrating portion 14. In this situation, a voltage is applied to the piezoelectric film 22 to vibrate the vibrating portion 14, as a result of which in the case where the viscosity of the fluid is large, the amplitude of the vibrating portion 14 becomes small whereas in the case where the viscosity of the fluid is small, the amplitude of the vibrating portion 14 becomes large, thereby being capable of measuring the viscosity of the fluid by detecting a current corresponding to that amplitude. Also, in the case where the viscosity of the fluid correlates with the concentration of the fluid or the density of components in the fluid, the concentration and the density of the fluid can be measured.

As one application of the above-described sensor device, there is a case in which the sensor device is built in a lead storage battery to measure a change in the density of an electrolyte. In other words, since a sulfuric acid aqueous solution is used as the electrolyte in the lead storage battery, and the viscosity of the sulfuric acid aqueous solution correlates with the density thereof, the density can be detected by the above sensor device. Also, since the density of the electrolyte changes depending on the charge and discharge of the battery, the charge and discharge state of the battery can be notified by measuring a change in the density.

FIG. 21 shows a state in which the above sensor device 40 is built in the lead storage battery. A porous sheet (separator) 34 is interposed between a pair of electrodes 32a and 32b of the battery, and the sensor device 40 is embedded in the porous sheet 34. The sensor device 40 in this state is accommodated within a battery case, and the electrolyte is injected thereinto in such a manner that the electrolyte is infiltrated into the porous sheet 34 so as to be fully supplied between the electrodes 32a and 32b, and the electrolyte that percolates from the porous sheet 34 enters the introduction holes 18, flows into the space 16 and is then led to the vibrating portion 14.

By the way, in order that the electrolyte is allowed to flow into the space 16 as described above, it is necessary that an air existing in the space 16 is exhausted to the exterior simultaneously, that is, the air is replaced by the flow-in electrolyte. However, in the conventional sensor device 40, when the sensor device 40 is built in the battery as shown in the figure, an opening end of the introduction holes 18 that communicate with the space 16 is in a state where it is in contact with the porous sheet 34. This makes it hard to discharge the air within the space 16, and the entrance of the electrolyte to the introduction holes 18 is irregular. As a result, there arises such a problem that it is difficult to replace the electrolyte by the air within the space 16 with the electrolyte.

SUMMARY OF THE INVENTION

The present invention has been made in view of the above problems with the prior art, and therefore an object of the present invention is to provide a sensor device which is capable of readily replacing an air by a fluid to be measured within a space.

In order to solve the above problems, according to the present invention, there is provided a sensor device which comprises: a base body having a vibrating portion; a piezoelectric element fixed onto one surface of said vibrating portion and having a piezoelectric film and a pair of electrodes which are in contact with said piezoelectric film; a space that allows a fluid to lead to the other surface of said vibrating portion; and introduction holes that communicate with said space; wherein said sensor device is in a longitudinal shape, and a recess which contains at least an opening end of the introduction hole on the surface side of the sensor device (a fluid flow-in side) in its region and extends up to the rear end portion of the sensor device is formed on the surface of the sensor device by a protrusion disposed on the surface of said sensor device so as to extend substantially continuously from the periphery of said introduction holes to a rear end portion of said sensor device (an end portion on a side far from said introduction holes).

Also, according to the present invention, there is provided a sensor device which comprises: a base body having a vibrating portion; a piezoelectric element fixed onto one surface of said vibrating portion and having a piezoelectric film and a pair of electrodes which are in contact with said piezoelectric film; a space that allows a fluid to lead to the other surface of said vibrating portion; and introduction holes that communicate with said space; wherein said sensor device is in a longitudinal shape, and a plurality of introduction holes are provided, and a first recess which contains at least opening ends of a part of introduction holes on the surface side of the sensor device in its region and extends continuously up to the rear end portion of the sensor device and a second recess which contains at least opening ends of other introduction holes on the surface side of the sensor device in its region are formed by a protrusion disposed on the surface of the sensor device, the protrusion is covered with a cap member in such a manner that a cylindrical space that opens only on a side of the rear end portion of the sensor device (an end portion on a side far from the introduction hole) is formed by said protrusion, said cap member and said first recess, and said first recess and said second recess are isolated from each other.

Further, according to the present invention, there is provided a sensor device which comprises: a base body having a vibrating portion; a piezoelectric element fixed onto one surface of said vibrating portion and having a piezoelectric film and a pair of electrodes which are in contact with said piezoelectric film; a space which is defined within said base body and allows a fluid to lead to the other surface of said vibrating portion; and introduction holes that communicate with said space; wherein said sensor device is in a longitudinal shape, and said space forms a cylindrical space and has a gas exhaust hole that opens on one end portion of said cylindrical space.

The above and other objects and features of the present invention will be more apparent from the following description taken in conjunction with the accompanying drawings.

BRIEF DESCRIPTION OF THE DRAWINGS

In the drawings,

FIGS. 1A and 1B are explanatory diagrams showing a sensor device in accordance with an embodiment of the present invention, in which FIG. 1A is a perspective view of the sensor device, and FIG. 1B is a partially enlarged cross-sectional view of the sensor device taken along a line I—I of FIG. 1A;

FIGS. 4A and 4B are explanatory diagrams showing a sensor device in accordance with still another embodiment of the present invention, in which FIG. 4A is a perspective view of the sensor device, and FIG. 4B is a partially enlarged cross-sectional view of the sensor device taken along a line II—II of FIG. 4A;

FIGS. 6A and 6B are explanatory diagrams showing a sensor device in accordance with still another embodiment of the present invention, in which FIG. 6A is a perspective view of the sensor device, and FIG. 6B is a partially enlarged cross-sectional view of the sensor device taken along a line III—III of FIG. 6A;

FIGS. 7A and 7B are explanatory diagrams showing a sensor device in accordance with still another embodiment of the present invention, in which FIG. 7A is a perspective view of the sensor device, and FIG. 7B is a partially enlarged cross-sectional view of the sensor device taken along a line IV—IV of FIG. 7A;

FIGS. 8A and 8B are explanatory diagrams showing a sensor device in accordance with still another embodiment of the present invention, in which FIG. 8A is a perspective view of the sensor device, and FIG. 8B is a partially enlarged cross-sectional view of the sensor device taken along a line V—V of FIG. 8A;

FIGS. 11A to 11C are explanatory diagrams showing a sensor device in accordance with still another embodiment of the present invention, in which FIG. 11A is a plan view of the sensor device, FIG. 11B is a cross-sectional view of the sensor device taken along a line VIII—VIII, and FIG. 11C is a cross-sectional view of the sensor device taken along a line VII—VII;

FIGS. 12A to 12C are explanatory diagrams showing a sensor device in accordance with still another embodiment of the present invention, in which FIG. 12A is a plan view of the sensor device, FIG. 12B is a cross-sectional view of the sensor device taken along a line VIII—VIII, and FIG. 12C is a cross-sectional view of the sensor device taken along a line VII—VII;

FIGS. 13A to 13C are explanatory diagrams showing a sensor device in accordance with still another embodiment of the present invention, in which FIG. 13A is a plan view of the sensor device, FIG. 13B is a cross-sectional view of the sensor device taken along a line VIII—VIII, and FIG. 13C is a cross-sectional view of the sensor device taken along a line VII—VII;

FIGS. 14A to 14C are explanatory diagrams showing a sensor device in accordance with still another embodiment of the present invention, in which FIG. 14A is a plan view of the sensor device, FIG. 14B is a cross-sectional view of the sensor device taken along a line VIII—VIII, and FIG. 14C is a cross-sectional view of the sensor device taken along a line VII—VII;

FIGS. 15A to 15C are explanatory diagrams showing a sensor device in accordance with still another embodiment of the present invention, in which FIG. 15A is a plan view of the sensor device, FIG. 15B is a cross-sectional view of the sensor device taken along a line VIII—VIII, and FIG. 15C is a cross-sectional view of the sensor device taken along a line VII—VII;

FIGS. 16A to 16D are explanatory diagrams showing a sensor device in accordance with still another embodiment of the present invention, in which FIG. 16A is a plan view of the sensor device, FIG. 16B is a cross-sectional view of the sensor device taken along a line VIII—VIII, FIG. 16C is a cross-sectional view of the sensor device taken along a line VII—VII, and FIG. 16D is a cross-sectional view of the sensor device taken along a line VII—VII;

FIGS. 17A to 17C are explanatory diagrams showing a sensor device in accordance with still another embodiment of the present invention, in which FIG. 17A is a plan view of the sensor device, FIG. 17B is a cross-sectional view of the sensor device taken along a line B—B, and FIG. 17C is a cross-sectional view of the sensor device taken along a line VII—VII;

FIGS. 18A to 18C are explanatory diagrams showing a sensor device in accordance with still another embodiment of the present invention, in which FIG. 18A is a plan view of the sensor device, FIG. 18B is a cross-sectional view of the sensor device taken along a line VIII—VIII, and FIG. 18C is a cross-sectional view of the sensor device taken along a line VII—VII;

FIGS. 19A to 19C are explanatory diagrams showing a sensor device in accordance with still another embodiment of the present invention, in which FIG. 19A is a plan view of the sensor device, FIG. 19B is a cross-sectional view of the sensor device taken along a line VIII—VIII, and FIG. 19C is a cross-sectional view of the sensor device taken along a line VII—VII;

FIGS. 20A and 20B are explanatory diagrams showing an example of conventional sensor device, in which FIG. 20A is a perspective view of the sensor device, and FIG. 20B is a partially enlarged cross-sectional view of the sensor device taken along a line VI—VI.

DETAILED DESCRIPTION OF THE PREFERRED EMBODIMENTS

Now, a description will be given in more details of preferred embodiments of the present invention with reference to the accompanying drawings.

Figure 1A:
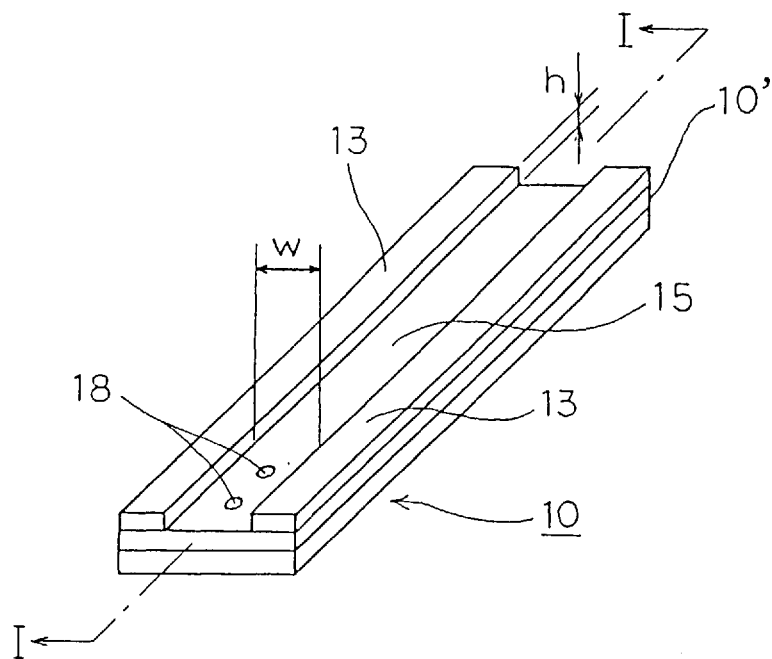
Figure 1B:
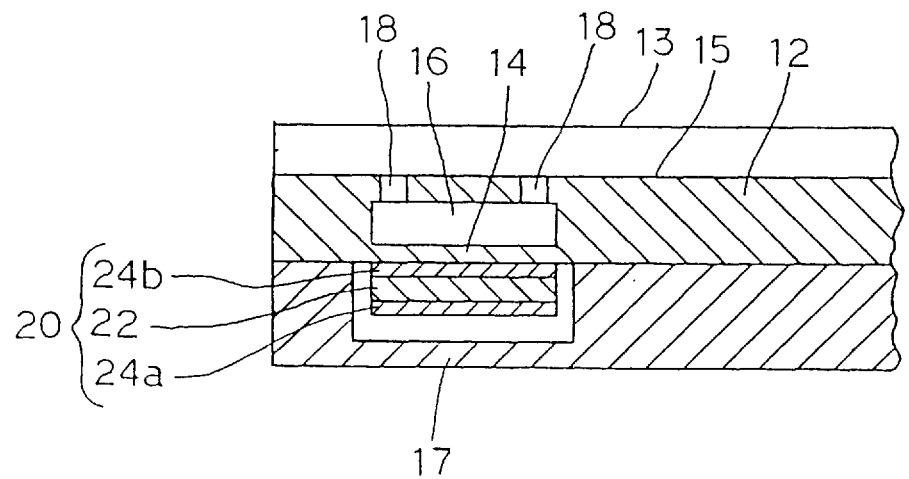

FIGS. 1A and 1B show an example of the sensor device of this type, in which FIG. 1A is a perspective view of the sensor device, and FIG. 1B is a partially enlarged cross-sectional view of the sensor device taken along a line I—I. As shown in the figures, a sensor device 10 according to the present invention includes, as its basic structure, a base body 12 having a vibrating portion 14, a piezoelectric element 20 fixed onto one surface of the vibrating portion 14 and having a piezoelectric film 22 and a pair of electrodes 24a and 24b which are in contact with the vibrating film 22, a space 16 that allows a fluid to lead to the other surface of the vibrating portion 14, and introduction holes 18 that communicate with the space 16, as in the above-mentioned conventional sensor device.

In addition to the above basic structure, the sensor device according to the present invention includes a protrusion 13 defined on the surface of the sensor device 10 as its characteristic structure. The protrusion 13 extends substantially continuously from the periphery of the introduction holes 18 to a rear end portion 10' of the sensor device (an end portion on a side far from the introduction holes 18), and is arranged to form a recess 15. The recess 15 contains at least opening ends of the introduction holes 18 on the surface side of the sensor device (a fluid flow-in side) within its recess formation region and is formed continuously up to the rear end portion 10' of the sensor device.

Figure 9:
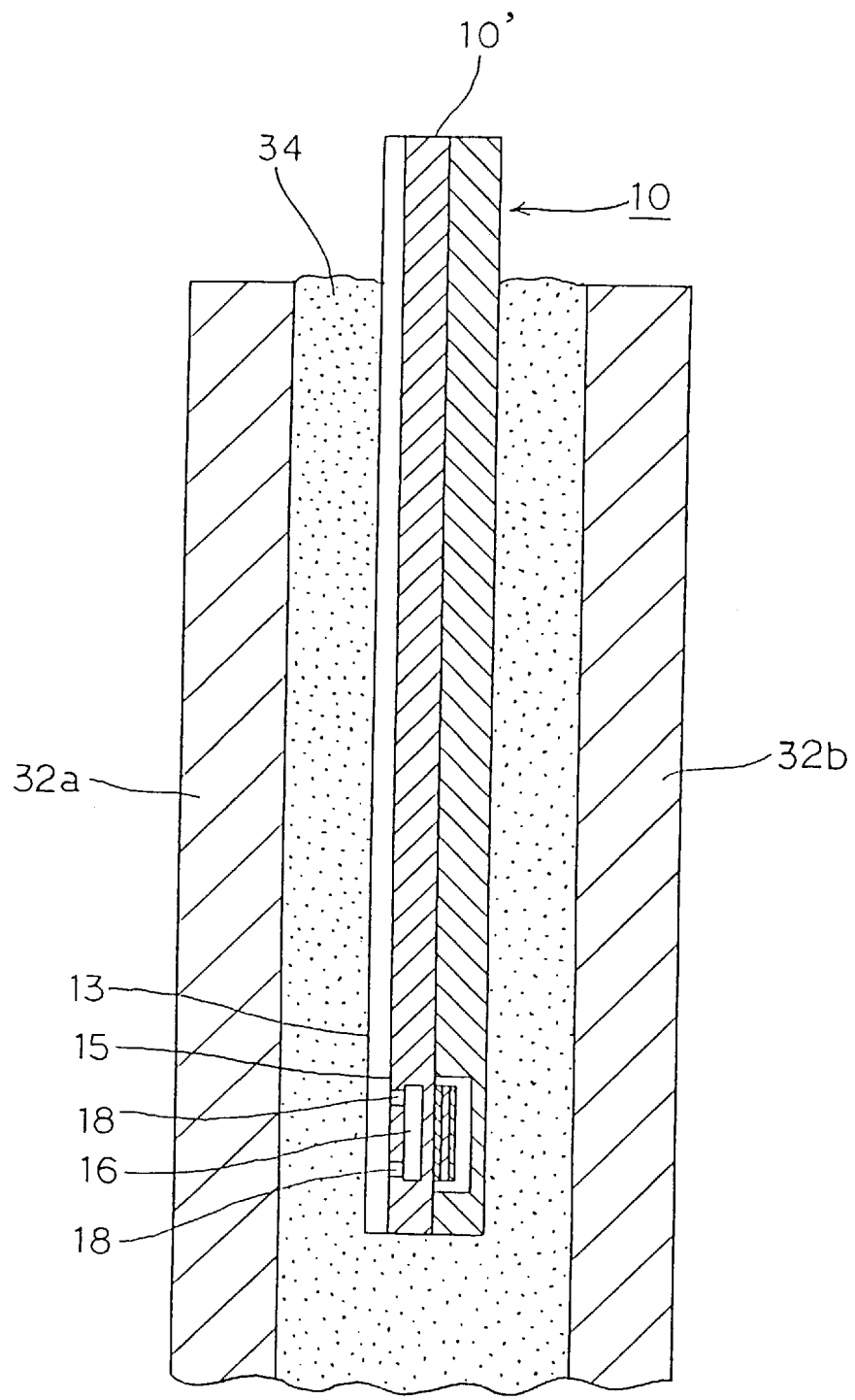
FIG. 9 is a cross-sectional view showing a state in which the sensor device of the present invention is built in a battery.

FIG. 9 shows a state in which the above sensor device 10 is built in a lead storage battery. The sensor device 10 is designed in such a manner that a tip portion where at least the introduction holes 18 are formed is embedded in the porous sheet 34 which is interposed between the electrodes 32a and 32b of the battery. In this case, the porous sheet 34 into which an electrolyte which is a fluid to be measured is infiltrated is in contact with the protrusion 13, but not in contact with the opening end of the introduction holes 18 on the surface side of the sensor device which is in the formation region of the recess 15. Also, the protrusion 13 allows a cylindrical space to be defined between the recess 15 and the porous sheet 34 so as to extend from the opening end of the introduction holes 18 toward the rear end 10' of the sensor device.

The cylindrical space allows the electrolyte that percolates from the porous sheet 34 to reside therein to regulate the entrance of the electrolyte into the introduction holes 18, and functions as a gas exhaust duct. In other words, the gas within the space 16 is exhausted from the introduction holes 18 to the above cylindrical space while the electrolyte flows in the space 16, thus readily replacing the gas by the electrolyte in the space 16.

In the present invention, the height h of the protrusion 13 defined on the surface of the sensor device is preferably 0.1 mm or more, and more preferably 0.3 mm or more. The width w of the recess 15 formed by the protrusion 13 is preferably 0.1 mm or more, and more preferably 0.5 mm or more. It should be noted that the height h and the width w of the protrusion 13 may not be constant with respect to the longitudinal direction of the sensor device 10, respectively. The height of the protrusion of the tip portion (the periphery of the introduction holes 18) of the sensor device is preferably higher for the response of the sensor. On the other hand, it is preferably lower for the introduction of the electrolyte into the introduction holes 18.

Figure 2:
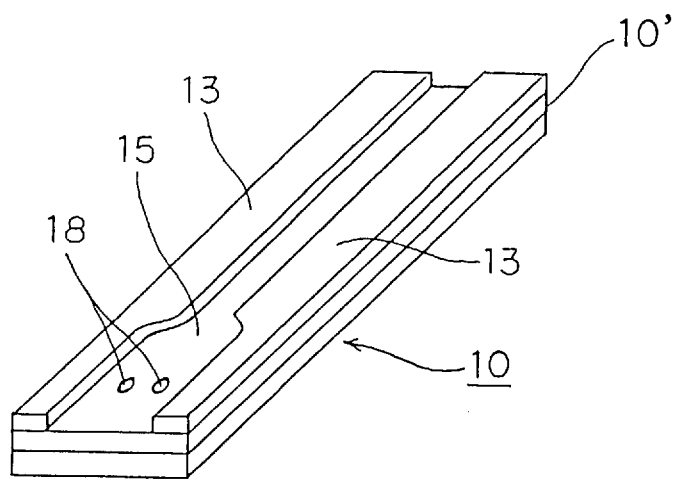
FIG. 2 is a perspective view showing a sensor device in accordance with another embodiment of the present invention.
Figure 3:
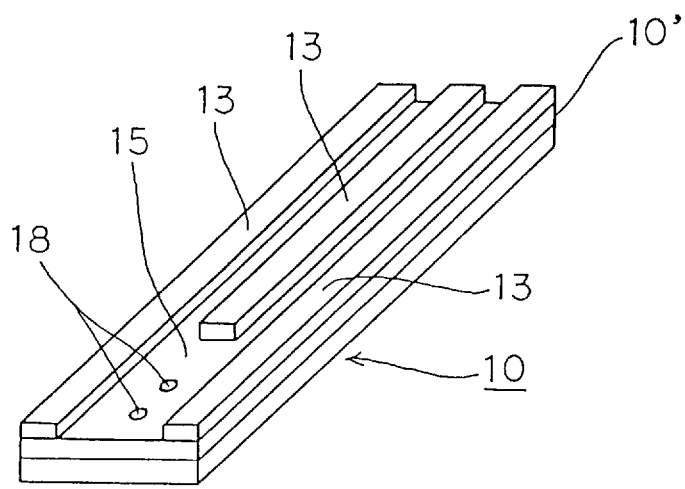
FIG. 3 is a perspective view showing a sensor device in accordance with still another embodiment of the present invention.

FIG. 2 shows a sensor device with the width of the recess 15 being changed in accordance with an embodiment of the present invention. FIG. 3 shows a sensor device with the recess 15 being branched by the protrusion 13 in accordance with another embodiment of the present invention. Taking the exhaust of a gas from the space 16 into consideration, it is preferable that a sectional area of the cylindrical space is increased. However, if the width of the recess is excessively wide, the porous sheet is inserted into the recess 15 so that the sectional area of the cylindrical space is adversely reduced. As shown in FIG. 3, if the recess 15 is branched, the respective widths of the branched portions are narrowed to prevent the porous sheet from being inserted into the recess 15. Also, the total sectional area of the cylindrical space in the respective branched portions can be increased.

As shown in FIG. 9, in the case where the sensor device 10 of the present invention is built in the battery, it is preferable that the sensor device 10 is not completely embedded in the porous sheet 34 in such a manner that its rear end portion (an end portion on a side far from the introduction holes 18) 10' is positioned in a space portion where no electrolyte exists. Since the recess 15 is formed continuously up to the rear end portion 10' of the sensor device, the rear end portion 10' of the sensor device 10 is positioned in the space where no electrolyte exists, thereby being capable of forming a passage that extends continuously from the space 16 to the space where no electrolyte exists. As a result, the gas within the space 16 is readily exhausted.

Figure 10:
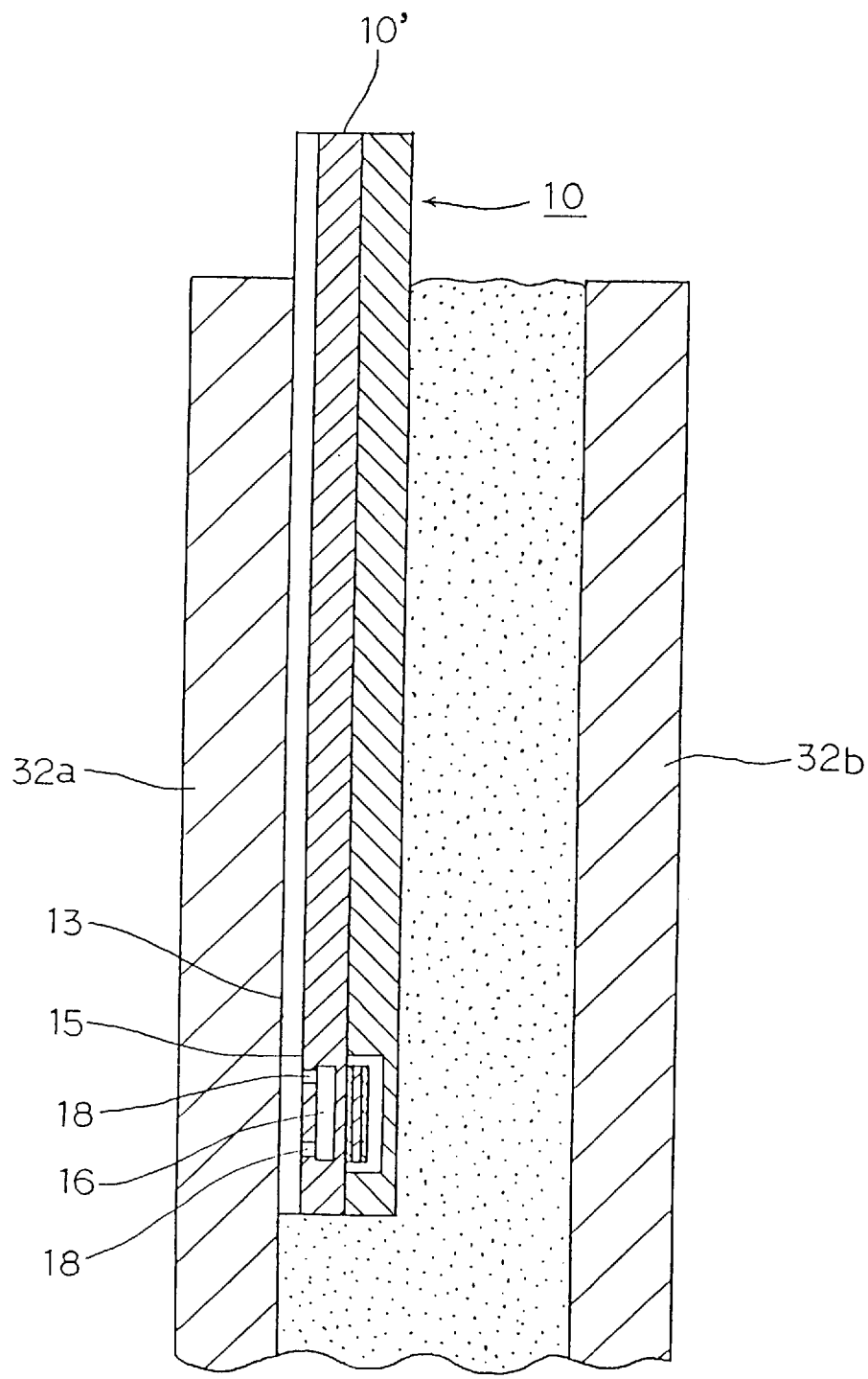
FIG. 10 is a cross-sectional view showing a state in which the sensor device of the present invention is built in a battery.

Also, as shown in FIG. 10, the sensor device 10 may be built in the battery in a state where one surface of the sensor device is in contact with the electrode of the battery. In this example, a surface of the sensor device 10 on a side where the protrusion 13 is provided is made in contact with the electrode 32a, and in this case, the cylindrical space is formed by an inner surface of the electrode 32a, the protrusion 13, and the recess 15. It should be noted that reversely to the example shown in FIG. 10, the sensor device 10 may be built in the battery in a state where the surface of the sensor device on a side where no protrusion 13 is formed is brought in contact with the electrode, but in the case where the height of the protrusion 13 is kept constant, it is preferable that the sensor device is arranged in such a manner that the protrusion 13 is in contact with the electrode as described above. This is because the space portion is sufficiently ensured.

Figure 4:
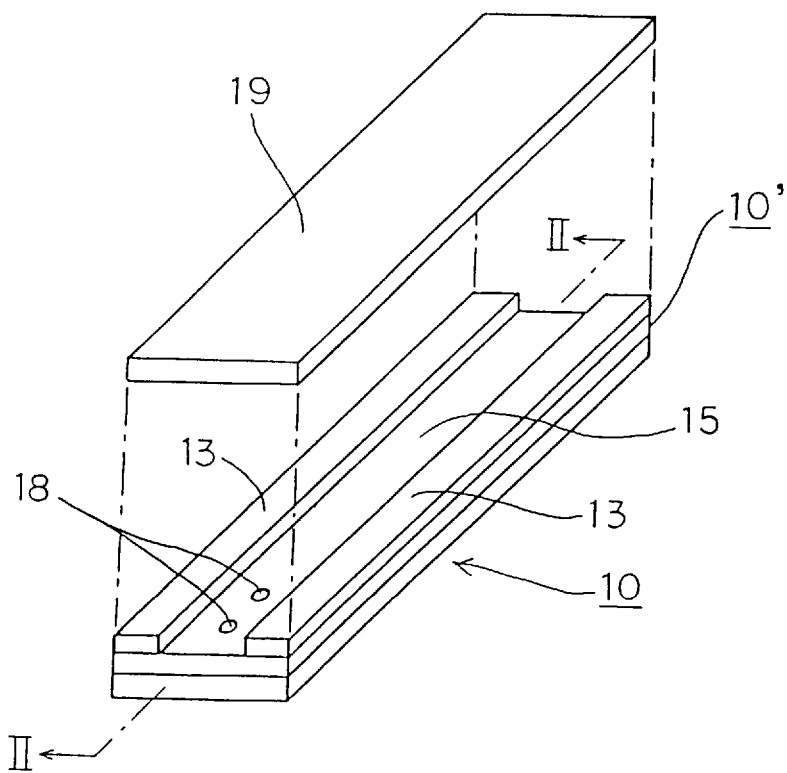
Figure 4:
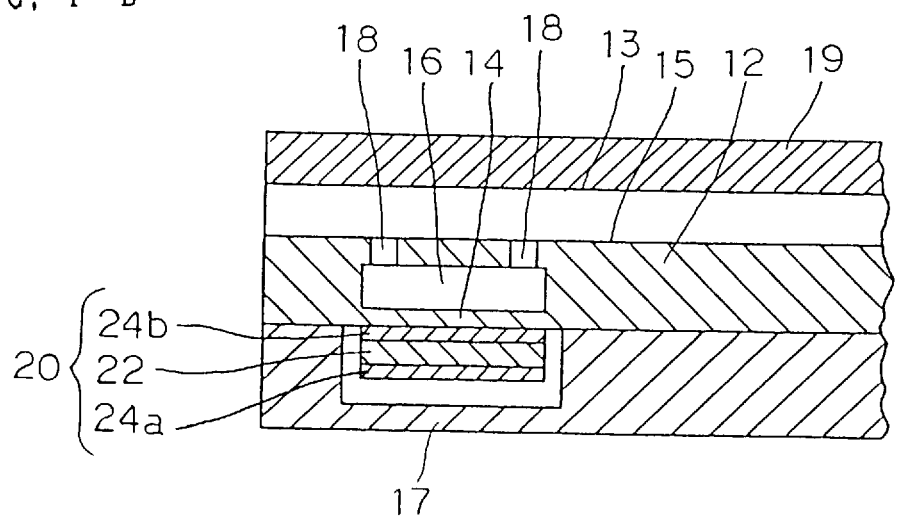

Further, in the present invention, as shown in the perspective view of FIG. 4A and the partially enlarged cross-sectional view of FIG. 4B which is taken along a line II—II of FIG. 4A, the protrusion 13 is covered with a cap member 19 so that the cylindrical space is formed by the protrusion 13, the cap member 19 and the recess 15. With the above structure, for example, when the sensor device is built in the battery, the porous sheet is prevented from being inserted into the recess to block the space, the gas exhaust space is ensured, and the degree of freedom for arranging the sensor device is increased.

Figure 5:
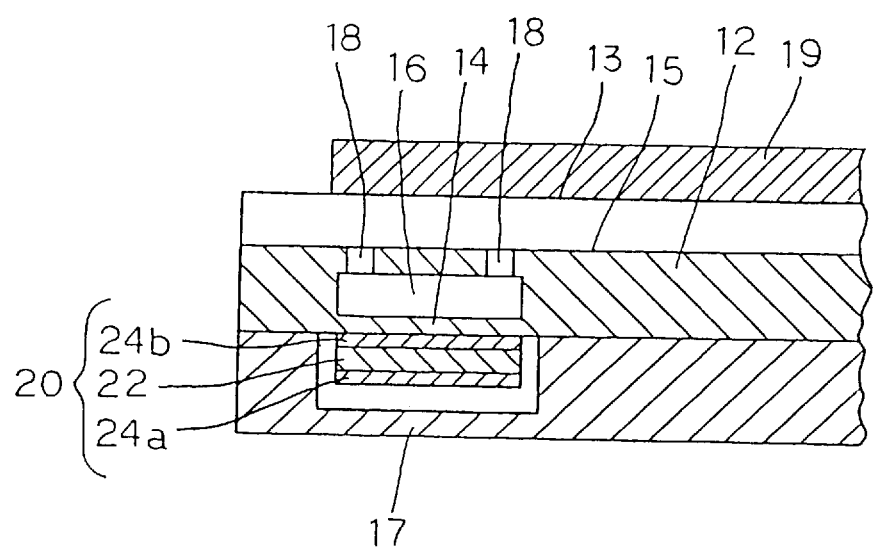
FIG. 5 is a partially enlarged cross-sectional view showing a sensor device in accordance with still another embodiment of the present invention.

It should be noted that it is not always necessary that the tip portion of the sensor device 10 is identical in position with the tip portion of the cap member 19, and as shown in FIG. 5, the tip portions of both the sensor device 10 and the cap member 19 may be shifted in position. However, it is preferable that at least one part of the introduction holes 18 is covered with the cap member 19 viewed from a lower surface side of the device. Also, the opening of the tip portion formed by the cap member 19 and the base body 12 is not always limited to the tip portion shown in the figure, and may be provided on the lateral side of the tip portion, and more preferably the opening is defined in a direction along which a plurality of introduction holes are aligned. Also, the thickness of the opening portion is preferably made smaller than that of the introduction holes for the introduction of a fluid to be measured.

Figure 6A:
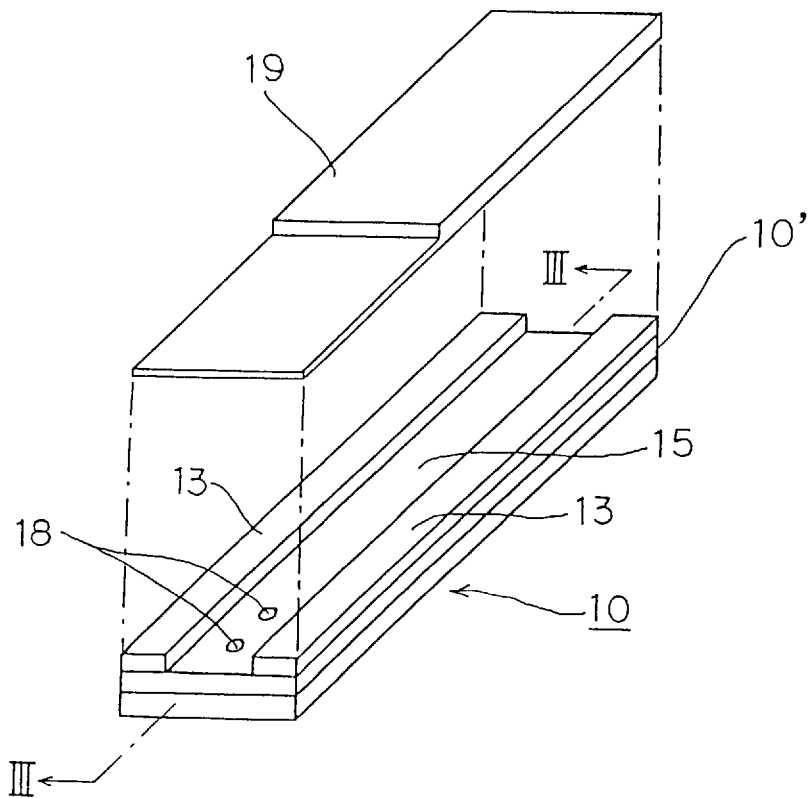
Figure 6B:
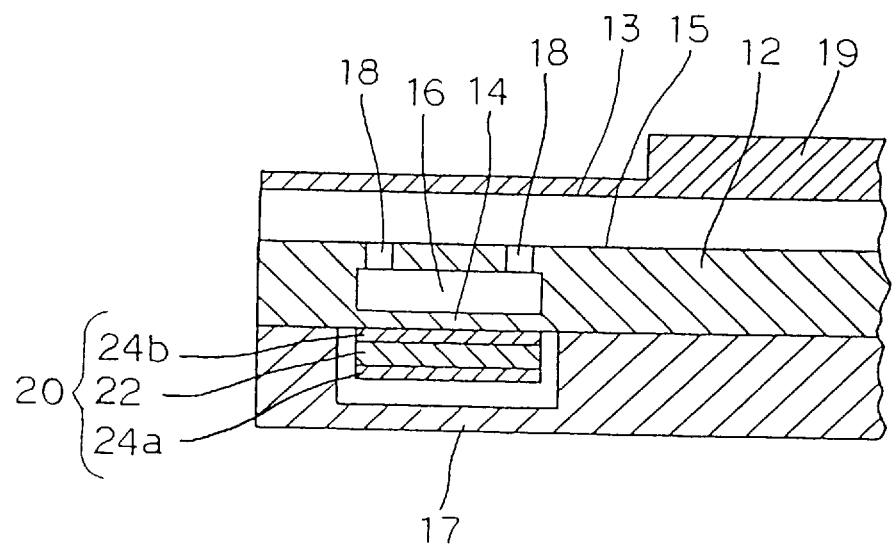

Further, it is not always necessary that the cap member 19 is uniform in thickness. For example, as shown in the perspective view of FIG. 6A and the partially enlarged sectional view of FIG. 6B which is taken along a line III—III of FIG. 6A, the thickness of the cap member 19 on the tip portion side of the sensor device may be thinned. In this case, machining is facilitated when changing the length of the cylindrical space formed in the tip portion of the sensor device.

Figure 7A:
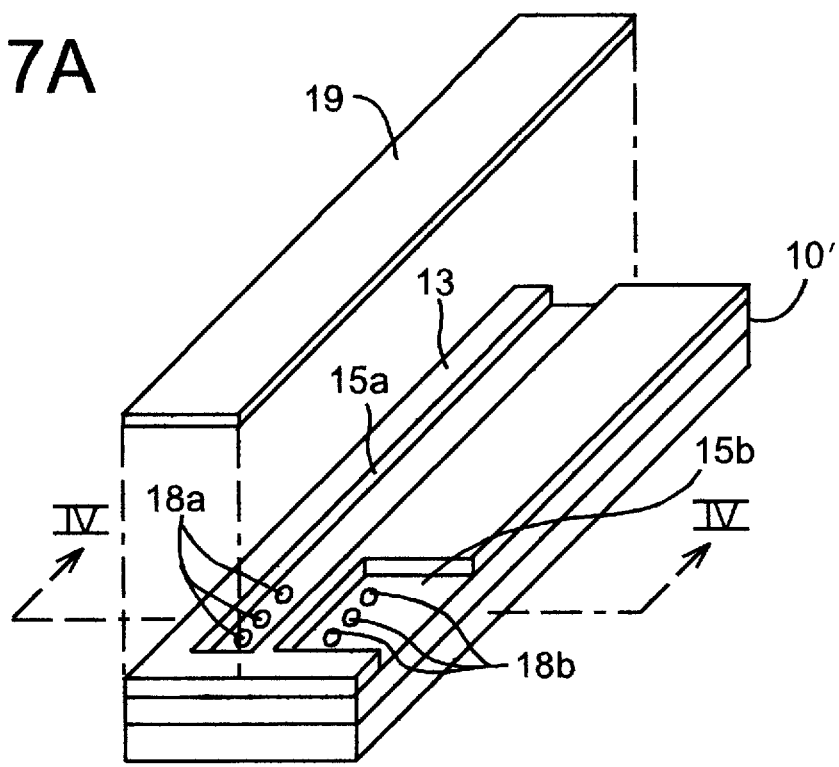
Figure 7B:
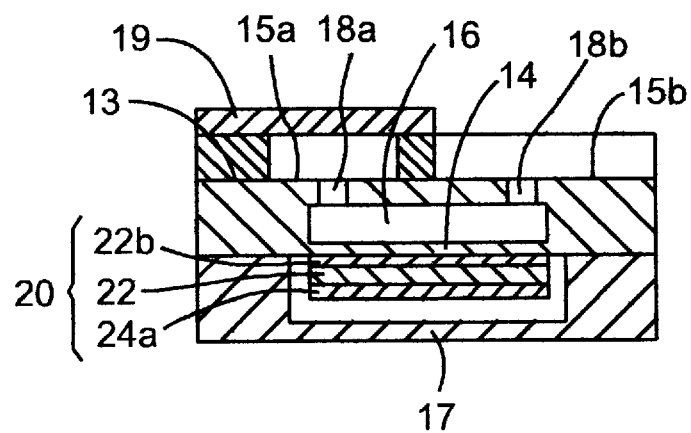

Furthermore, according to the present invention, as a sensor device which can surely and readily replace the gas by the electrolyte in the space, there is provided a sensor device with the structure shown in the perspective view of FIG. 7A and the cross-sectional view of FIG. 7B which is taken along a line IV—IV of FIG. 7A. Similarly to the above sensor device, this sensor device has a protrusion 13 on the surface of the sensor device to form a recess. However, this sensor device has two discontinuous recesses consisting of a first recess 15a and a second recess 15b.

Also, the sensor device 10 includes a plurality of introduction holes, and the first recess 15a contains the opening ends of introduction holes 18a which are parts of the plural introduction holes 18 on the surface side of the sensor device in its region, and extends continuously up to the rear end portion of the sensor device (an end portion on a side far from the introduction holes) 10'. On the other hand, the second recess 15b is formed so as to contain the opening ends of at least introduction holes 18b which are parts of other introduction holes on the surface side of the sensor device in its region.

The protrusion 13 is covered with a cap member 19, and a cylindrical space is formed by the protrusion 13, the cap member 19, and the first recess 15a. The cylindrical space is opened on only a side of the rear end portion 10' of the sensor device. The first recess 15a and the second recess 15b are discontinuously formed and isolated from each other by the protrusion 13 and the cap member 19.

The sensor device 10 thus structured is built in the battery in such a manner that its rear end portion 10' is positioned in a space where no electrolyte exists, and then an electrolyte is injected thereinto. As a result, the electrolyte percolated from the porous sheet resides in the second recess 15b and enters the introduction holes 18b so that it flows into the space 16. However the electrolyte does not enter the cylindrical space formed by the protrusion 13, the cap member 19, and the first recess 15a. Hence, with the introduction holes 18a being not blocked by the electrolyte, a gas within the space 16 is surely exhausted to the cylindrical space through the introduction holes 18a while the electrolyte flows into the space 16 from the introduction holes 18b.

In other words, in the sensor device of this example, the plural introduction holes are divided into introduction holes 18b for leading the electrolyte to the space 16 and introduction holes 18a for exhausting the gas within the space 16 so that their roles are shared. As a result, the replacement of the air in the space by the electrolyte is more surely and readily conducted.

Figure 8:
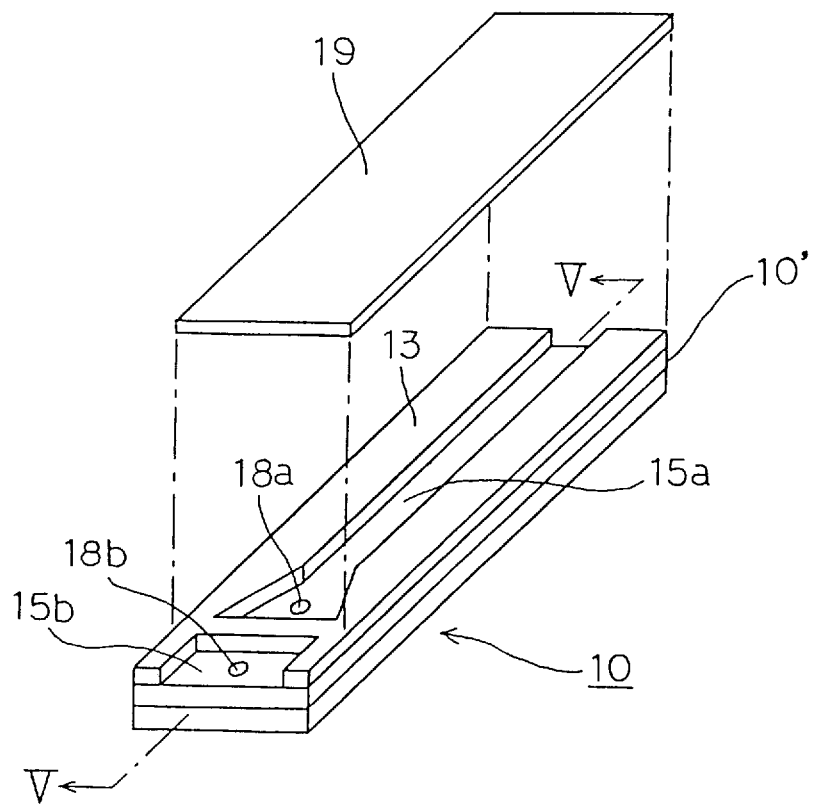
Figure 8:
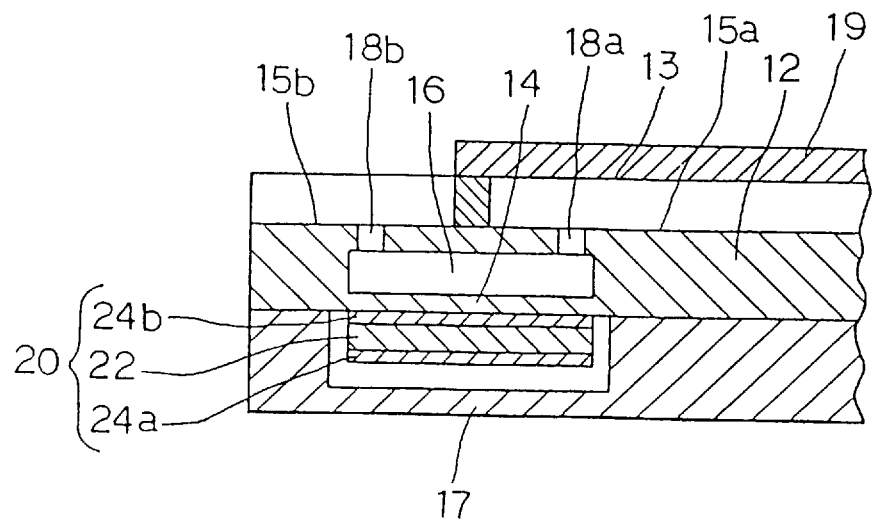

FIGS. 8A and 8B are a perspective view showing a sensor device in accordance with another embodiment of the present invention, and a partially enlarged sectional view showing the sensor device taken along a line V—V of FIG. 8A. In the figures, a first recess 15a and a second recess 15b are arranged in a longitudinal direction of the sensor device 10, and the respective recess formation regions are structured in such a manner that the open ends of introduction holes 18a and 18b on the surface side of the sensor device are contained in their recess formation regions one by one, respectively.

Then, in the present invention, as shown in FIGS. 11 to 16, there can be formed a sensor device of the structure in which a space forms a cylindrical space, and which has a gas exhaust port opening on its one end portion.

In the sensor device 10 of this structure, a space 16 formed within the base body 12 forms a cylindrical space, and there is provided a gas exhaust hole 26 which opens on one end portion of the space 16 (cylindrical space). It should be noted that reference numeral 28 denotes a gas exhaust hole 26 for introducing a fluid into the space 16. FIGS. 11A, 12A, 13A, 14A, and 15A are a plan view showing a different sensor device, respectively; FIGS. 11B, 12B, 13B, 14B, and 15B are a cross-sectional view showing the sensor device taken along a line VIII—VIII, respectively; and FIGS. 11C, 12C, 13C, 14C, and 15C are a cross-sectional view showing the sensor device taken along a line VII—VII. FIG. 16A is a plan view showing another sensor device, FIG. 16B is a cross-sectional view showing the sensor device taken along a line VIII—VIII, FIG. 16C is a cross-sectional view showing the sensor device taken along a ling VII—VII, and FIG. 16D is a cross-sectional view showing the sensor device taken along a line VII—VII.

Those sensor devices 10 are built in a lead storage battery in such a manner that the rear end portion 10' is positioned in a space where no electrolyte exists, and then an electrolyte is injected therein. As a result, the electrolyte flows from the introduction holes 28, and a gas within the space 16 elevates in the cylindrical space of the space 16 and is then exhausted to the exterior from the gas exhaust hole 26 that opens on an upper end portion of the cylindrical space while the electrolyte flows into the space 16.

Figure 11B:
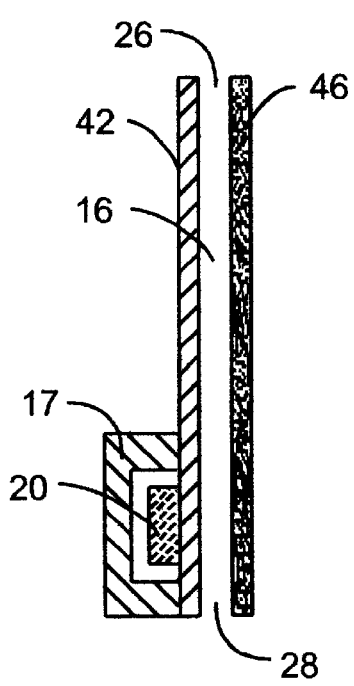
Figure 11A:
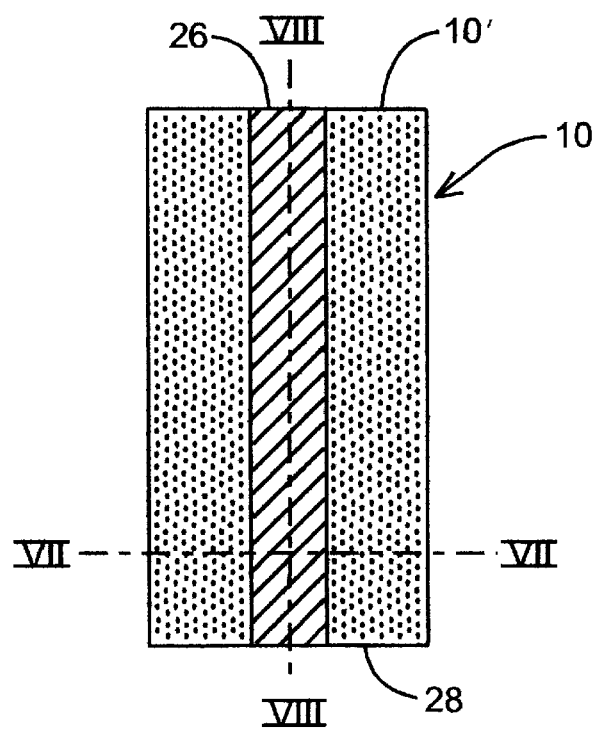
Figure 11C:
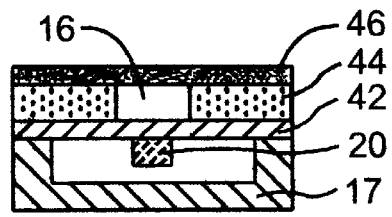
Figure 12B:
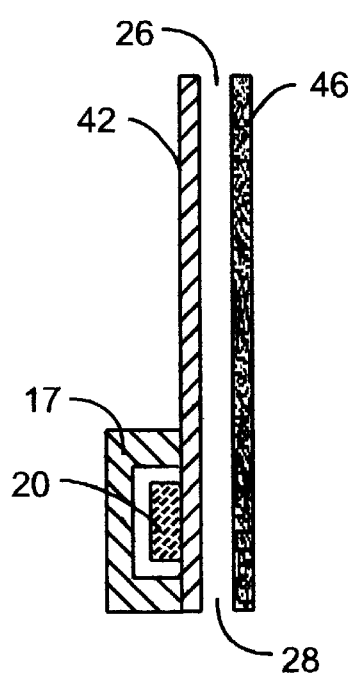
Figure 12A:
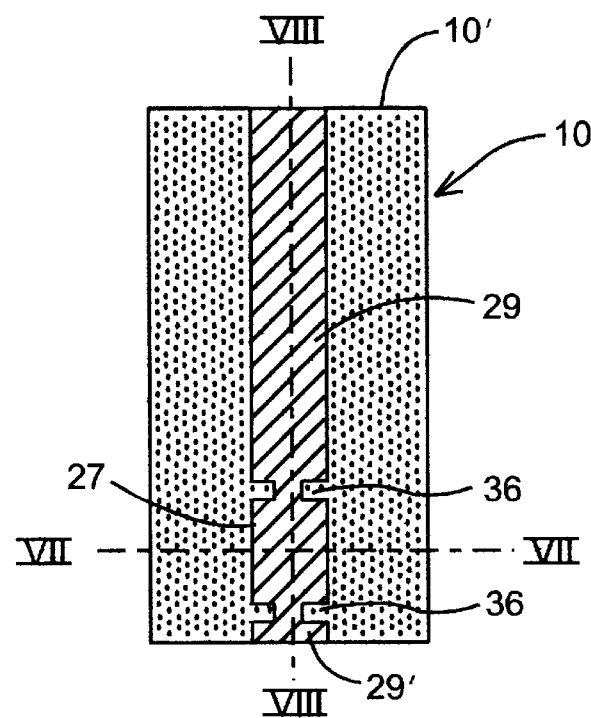
Figure 12C:
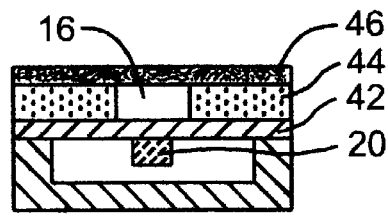
Figure 13B:
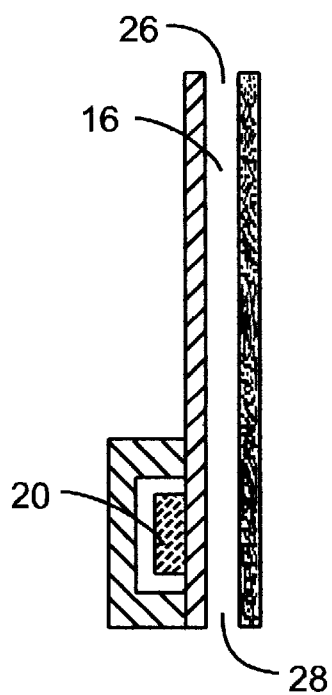
Figure 13A:
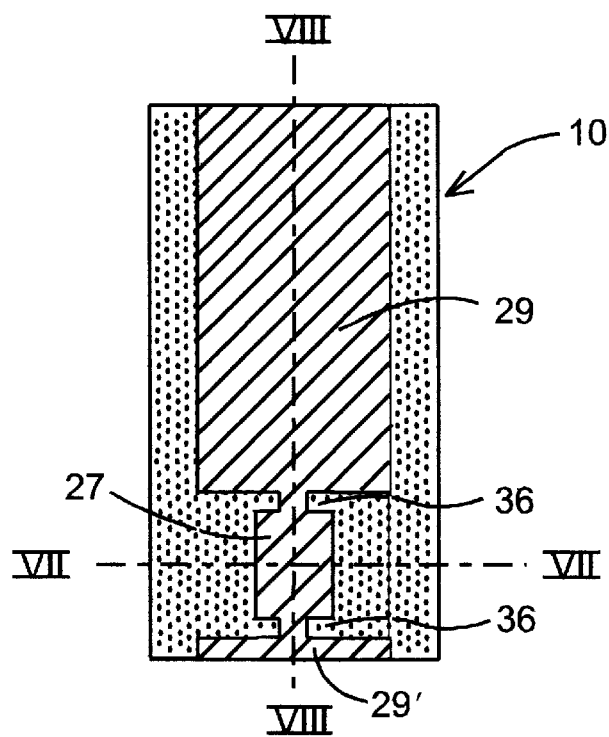
Figure 13C:
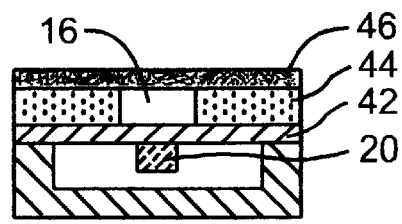
Figure 14B:
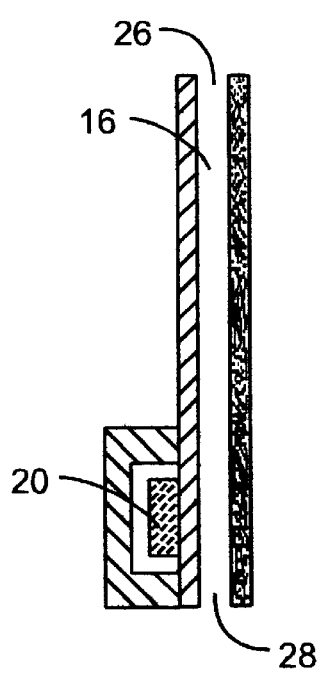
Figure 14A:
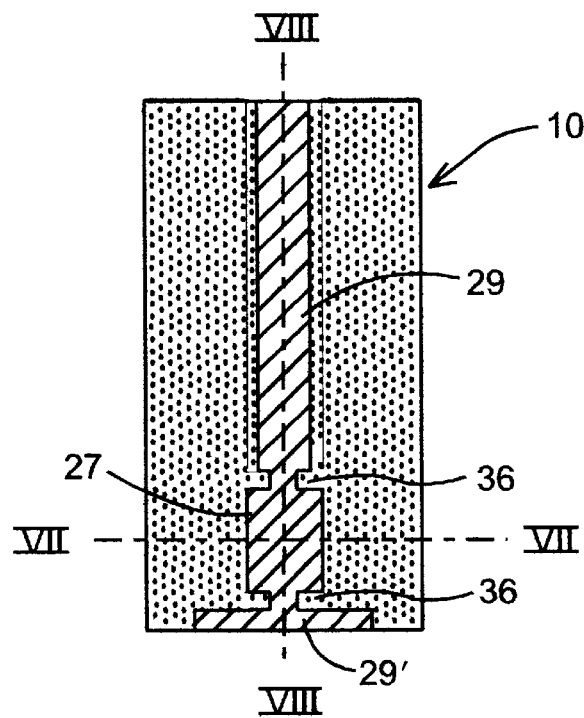
Figure 14C:
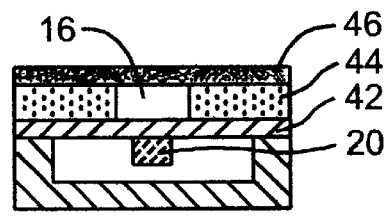

FIGS. 11A to 11C show a basic structure of a sensor device in which a space forms a cylindrical space, which is an example in which a space 16 forms a simple cylindrical space. A sensor device shown in FIGS. 12A to 12C is an example in which drawing portions are formed as a space 16 on the boundaries of a part 27 corresponding to the piezoelectric element 20 and other parts 29, and 29'. The sensor devices shown in FIGS. 13A to 13C and 14A to 14C show modified examples of FIGS. 12A to 12C, respectively. FIGS. 13A to 13C show an example in which lateral sectional areas of parts 29 and 29' of the space 16 except for a part corresponding to the piezoelectric element 20 are enlarged in comparison with that of a part 27 corresponding to the piezoelectric element 20, and FIGS. 14A to 14C show an example in which a lateral sectional area of a part 29' of the space 16 which communicates with the communication holes 28 is enlarged whereas a lateral sectional area of a part 29 of the space 16 which communicates with the gas exhaust hole 26 is reduced.

Figure 15B:
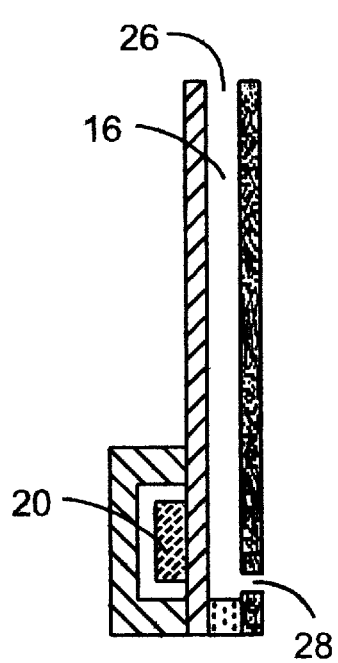
Figure 15A:
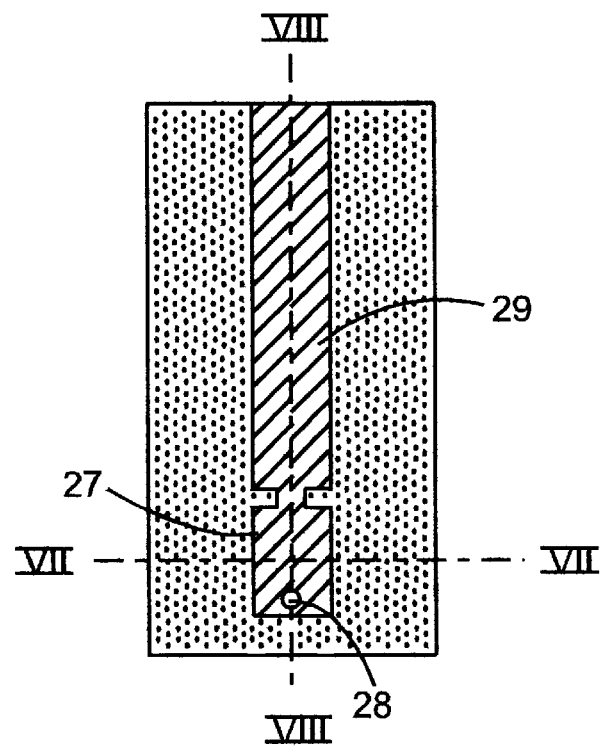
Figure 15C:
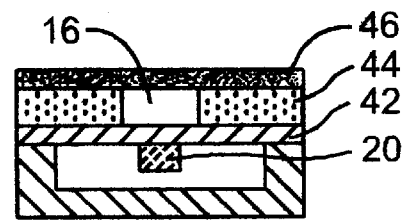
Figure 16B:
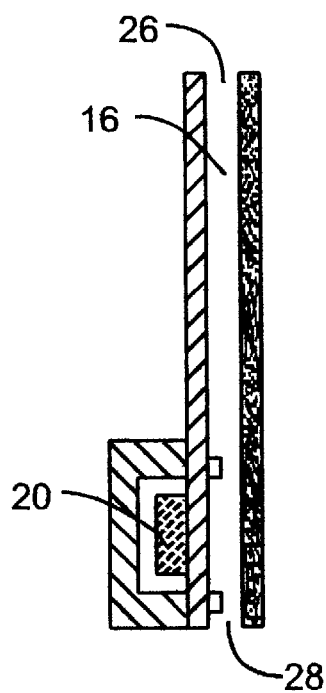
Figure 16A:
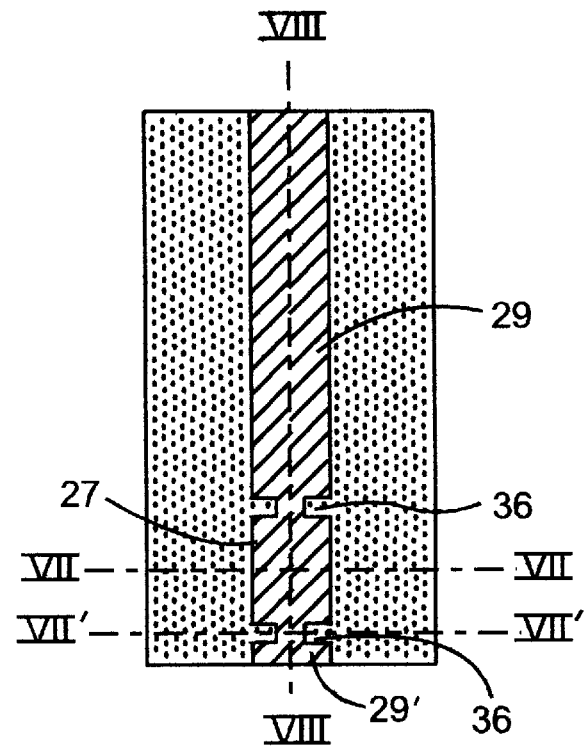
Figure 16C:
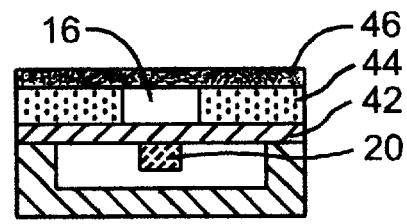
Figure 16D:
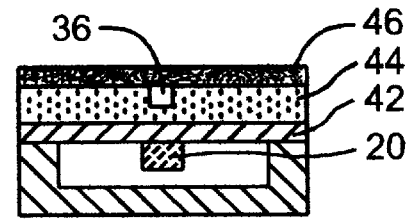

A sensor device shown in FIGS. 15A to 15C show an example in which an introduction hole 28 that communicates with the space 16 is defined not in a lower end portion of the cylindrical space but in a lateral side of the lower end portion thereof. A sensor device shown in FIGS. 16A to 16D show an example in which the lateral sectional areas of the drawing portion 36 are more reduced in FIG. 12.

The provision of the drawing portions 36 on the boundaries of the part 27 corresponding to the piezoelectric element 20 and other parts 29, 29' makes it difficult that a fluid within the part 27 is adversely affected by a change in an external environment such as vibrations, thereby being capable of more surely holding the function of a sensor.

According to the sensor devices shown in FIGS. 11A to 16D, since they are of the structure in which the space forms the cylindrical space, they have such an advantage that a manufacture process is simplified in comparison with the structure in which the protrusion is provided, or the structure in which the protrusion and the cap member are provided, as shown in FIGS. 1A to 8B. In addition, because the shape of a flow passage of a fluid which extends from the introduction holes 28 up to the gas exhaust hole 26 through the space 16 is straight, the gas within the space 16 is more readily exhausted.

Furthermore, the sensor devices shown in FIGS. 11A to 16D facilitate the control of the resistance of the fluid to the flow passage in comparison with the sensor devices shown in FIGS. 1A to 8B. In other words, in the sensor devices shown in FIGS. 1A to 8B, in the case where the resistance to the flow passage is controlled by a diameter of the introduction holes 18 and a thickness of a member that forms the introduction holes 18, in order to measure a fluid of a low viscosity, it is required that the diameter of the introduction holes 18 is reduced and the thickness of the member is increased. However, there arises such problems that the reduction of the diameter of the introduction holes 18 is limited from the viewpoint of the machining accuracy, and also that the sensor device can not be thinned.

On the other hand, in the sensor devices shown in FIGS. 11A to 16D, because the space 16 that regulates the resistance to the flow passage is a cylindrical space formed in the base body 12, the resistance to the flow passage can be readily controlled by adjusting the sectional area and the length of the space 16 depending to the characteristics of the fluid to be measured such as viscosity, and in particular, even in the case where the space 16 is lengthened to increase the resistance to the flow passage, the sensor device can be thinned.

Figure 17B:
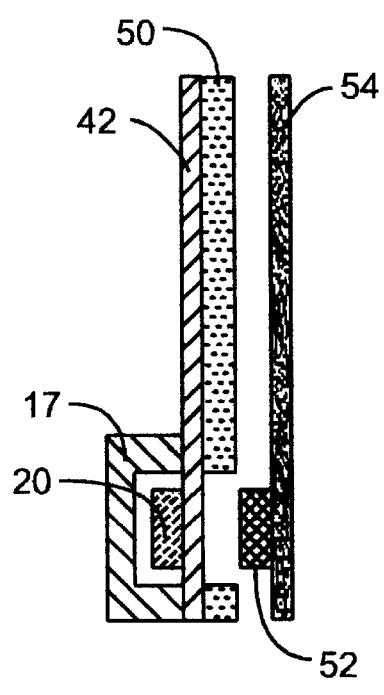
Figure 17A:
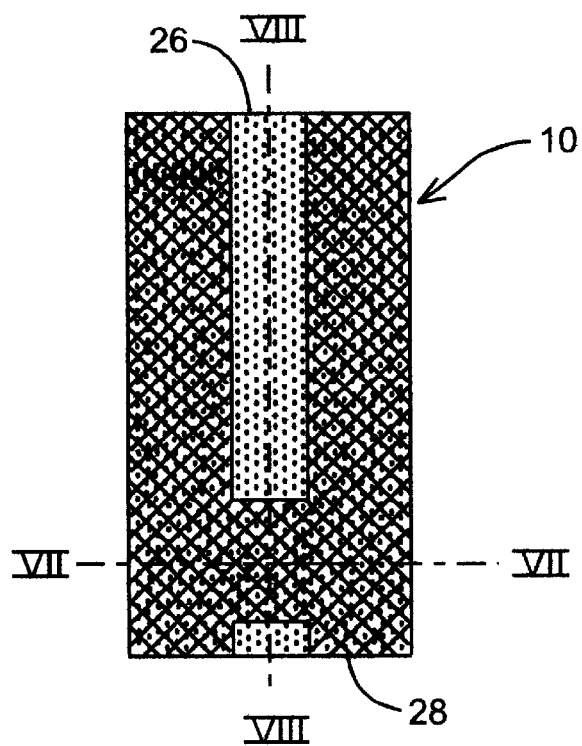

FIGS. 17A to 19C show examples of a four-layer structure which is thickened by one layer more than the sensor devices shown in FIGS. 11A to 16D as a layer structure that constitutes a base body 12 having a space 16 formed inside thereof. It should be noted that FIGS. 17A, 18A, and 19A show plan views of the sensor devices, FIGS. 17B, 18B, and 19B show cross-sectional views taken along a line VIII—VIII of FIGS. 17A, 18A, and 19A, and FIGS. 17C, 18C and 19C show cross-sectional views taken along a line VII—VII thereof, respectively.

The sensor devices shown in FIGS. 11A to 16D usually have, as a layer structure that constitutes the base body 12, a three-layer structure consisting of a first layer 42 of a thin plate layer which forms the vibrating portion 14 a part of which is arranged to fix the piezoelectric element 20, a second layer 44 having a window that forms the space 16 after sintering the laminated layers, and a third layer 46 that shields the window. In this case, the second layer 44 having the window is formed on the first layer 42 of the thin plate layer, and the second layer 44 and the third layer 46 are held by the first layer 42 weak in strength. Therefore, in the sensor devices shown in FIGS. 17A to 19C, a second layer 50 having a window (which forms the space 16 after the laminated layers are sintered) at only a part 27 corresponding to the piezoelectric element 20 is located on the first layer 42 that forms the thin plate layer, then a third layer 52 having a window (which forms a cylindrical space after the laminated layers are sintered) which communicates with the space 16 is laminated on the second layer 50, and further a fourth layer 54 that shields the window that forms the cylindrical space is laminated on the third layer 52. With the above structure, the second layer 50 that functions as a backup layer is provided on the first layer 42 of the thin plate layer except for the part 27 corresponding to the piezoelectric element 20, as a result of which the sensor device is obtained which improves in strength and durability as a whole.

Figure 17C:
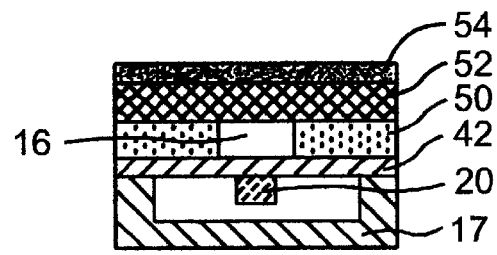
Figure 18B:
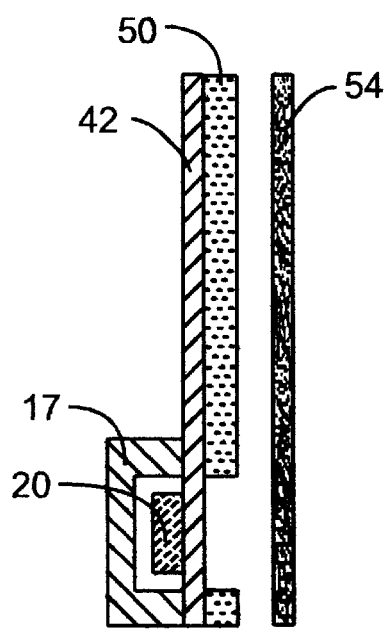
Figure 18A:
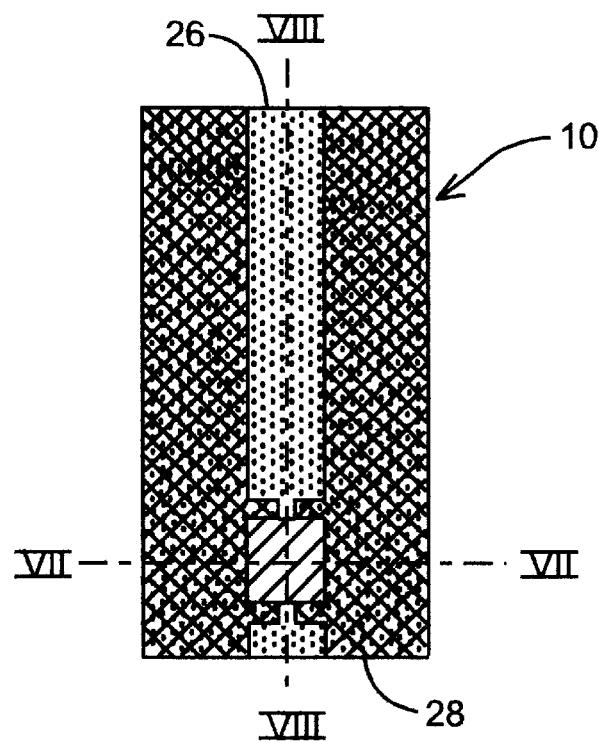
Figure 18C:
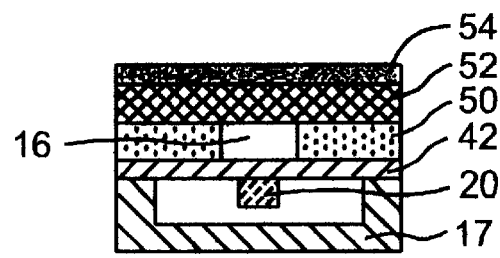
Figure 19B:
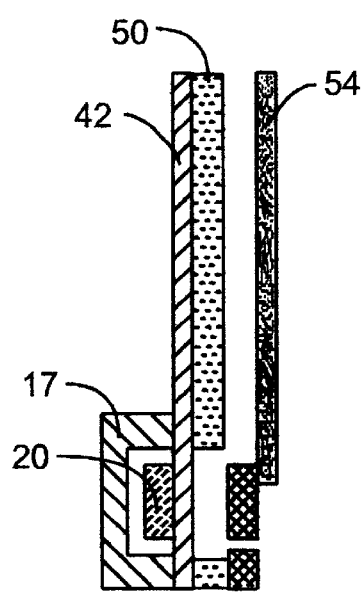
Figure 19A:
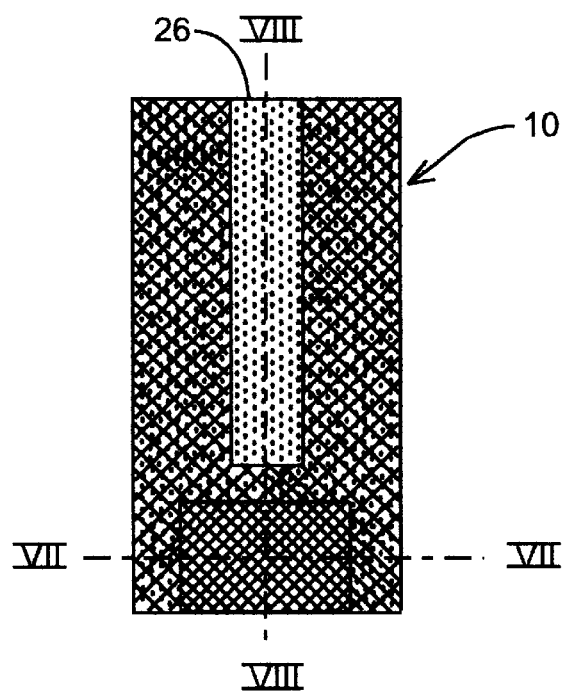
Figure 19C:
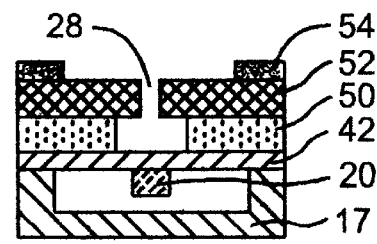
Figure 20A:
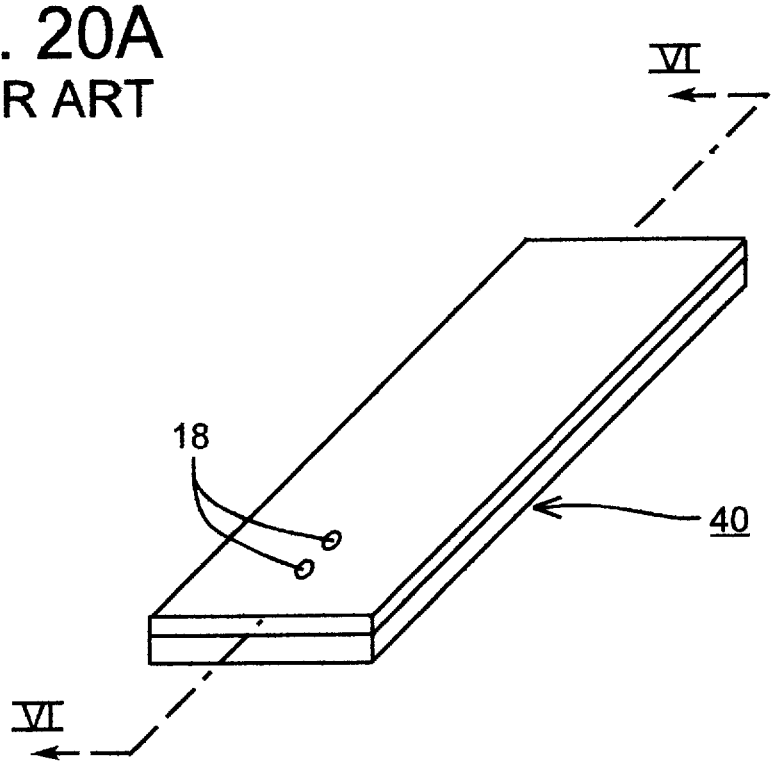
Figure 20B:
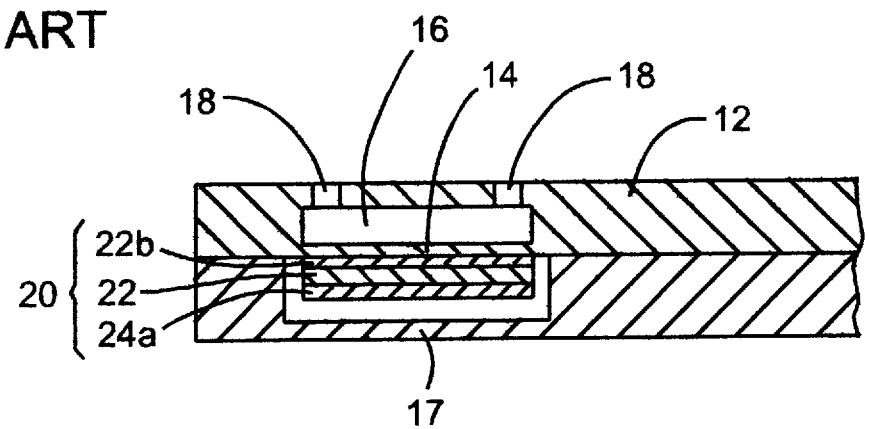
Figure 21:
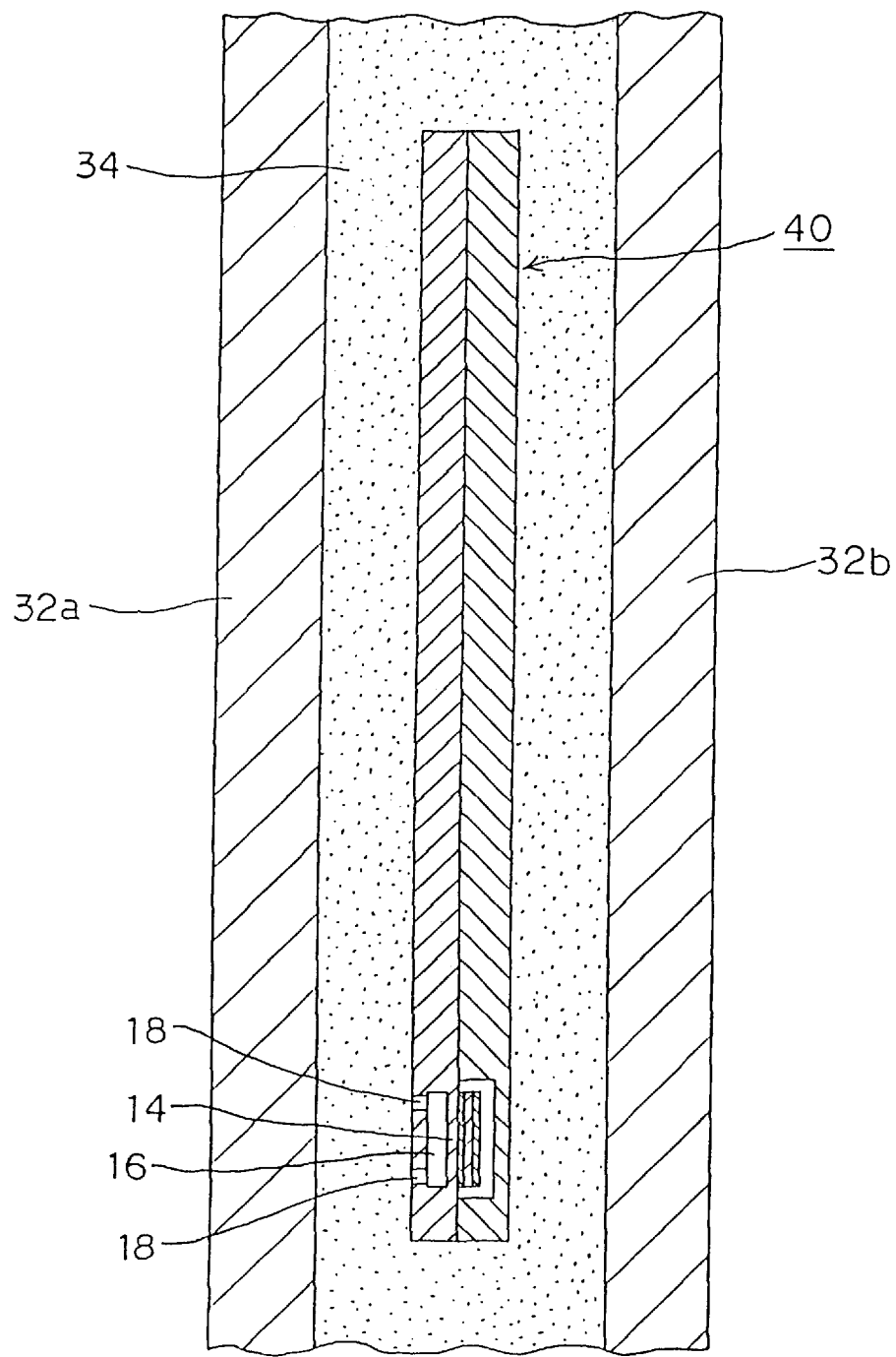
FIG. 21 is a cross-sectional view showing a state in which the conventional sensor device is built in a battery.

The sensor device shown in FIGS. 17A to 17C shows an example in which only the window and a part that communicates with the space 16 are spatial in the third layer 52 having the window that communicates with the space 16. The sensor device shown in FIGS. 18A to 18C show an example in which the window and a part corresponding to the piezoelectric element 20 are spatial, and a slender communication space is provided between the window and a part corresponding to the piezoelectric element 20 in the third layer 52 having the window that communicates with the space 16. Further, the sensor device shown in FIGS. 19A to 19C show an example in which only a part that communicates with the space 16 is spatial in the third layer 52 having the window that communicates with the space 16, and a part corresponding to the piezoelectric element 20 is not shielded, and an introduction hole 28 that extends to the space 16 is formed in the fourth layer 54 that shields the window.

It should be noted that the part corresponding to the piezoelectric element 20 is preferably arranged at a relatively lower position. In other words, the piezoelectric element part is disposed at the relatively lower position in the sensor device with the advantages stated below. In the case where the sensor device is built in the battery, the amount of electrolyte is small, the piezoelectric element part can be filled with such electrolyte. Even though the electrolyte is sucked out, the piezoelectric element part becomes empty last, thus making it hard for the electrolyte to escape. Further, the adhesion of the electrolyte to a wall surface forming the cylindrical space, which is caused on a portion upper than the piezoelectric element part, acts as a resistance to a suck-out force, thereby making it hard for the electrolyte to escape.

The above description was given of the example in which the sensor device of the present invention is built in the lead storage battery. However, the sensor device of the present invention is not limited to such application, but may be applicable to a case in which the sensor device is built in another sort of battery, or a case except that it is built in the battery. It is needless to say that the fluid to be measured is not limited to the electrolyte. That is, the sensor device of the present invention can be used to measure various kinds of fluid characteristics of a variety of fluids such as acid-base solvent, a variety of aqueous, solvent using an organic solvent or an organic solvent per se.

Subsequently, a description will be given in more detail of the structure of the respective components in the sensor device of the present invention.

In the present invention, the space 16 is defined in the base body 12 so that the vibrating portion 14 is thinned, and the introduction hole 18 that communicates with the space 16 is also defined in the base body 12. The shape of the space 16 is not particularly limited.

The vibrating portion 14 is preferably in the form of a plate because it is proper for vibrations. In this case, the thickness of the plate is preferably set to 1 to 100 μm, more preferably to 3 to 50 μm, and most preferably to 5 to 20 μm. When the thickness of the plate exceeds 100 μm, the sensitivity is deteriorated, and when it is less than 1 μm, the mechanical strength is deteriorated.

The piezoelectric element 20 is fixed onto one surface of the vibrating portion 14 (a surface opposite to a side facing the space 16). The piezoelectric element 20 includes the piezoelectric film 22 and a pair of electrodes 24a, 24b which are in contact with the piezoelectric film 22. When a voltage is applied to the piezoelectric film 22 through the pair of electrodes 24a and 24b, dielectric polarization is developed so that the piezoelectric element 20 flexibly vibrates in the width direction of the piezoelectric film 22 and the vibrating portion 14 together with the vibrating portion 14.

The thickness of the piezoelectric film 22 is preferably set to 1 to 100 μm, more preferably to 5 to 50 μm, and most preferably to 5 to 30 μm. When the thickness of the piezoelectric film 22 exceeds 100 μm, the sensitivity is deteriorated, and when it is less than 1 μm, it is difficult to ensure the reliability.

The piezoelectric film 22 may be dense or porous, and when it is porous, the porosity is preferably set to 40% or less. Also, the piezoelectric film 22 may be formed of one layer or of a laminate structure consisting of two or more layers. When it is of the laminate structure consisting of two or more layers, the respective layers may be laterally located, or vertically located. The thickness of electrodes 24a and 24b is set appropriately depending on its application, but preferably set to 0.1 to 50 μm.

The piezoelectric element 20 is normally covered with the protective cover 17. In the case of measuring a fluid of strong acid such sulfuric acid or strong base such as sodium hydroxide aqueous, the protective cover 17 enables the piezoelectric element 20 to be isolated from those fluids.

In the sensor device according to the present invention, a voltage is applied to the piezoelectric element to vibrate the piezoelectric element and the vibrating portion, thereby vibrating a fluid which is in contact with the vibrating portion. Then, the piezoelectric film of the piezoelectric element converts the vibrations into electric signals, and then outputs the electric signals through the electrode which is disposed in contact with the piezoelectric film. For example, a voltage is applied to the piezoelectric element 20 to vibrate the piezoelectric element 20 and the vibrating portion 14 while being in contact with the fluid.

Then, a current is detected through the electrodes 24a and 24b of the piezoelectric element 20, to thereby obtain information relating to values of the impedance, phase, resistance, reactance, admittance, conductance, susceptance, inductance, capacitance, loss coefficient, etc., of the piezoelectric element 20, as well as the value of a frequency (resonance frequency) corresponding to those values. Since those information correlates with the characteristics such as the viscosity of the fluid, such characteristics of the fluid can be detected.

In the present invention, the base body 12 having the vibrating portion 14 is preferably made of ceramics. For example, stabilized zirconia, alumina, magnesia oxide, mullite, aluminum nitride, silicon oxide, glass, or the like can be used for the material of the base body 12. The stabilized zirconia is preferable because even though the vibrating portion is thin, the mechanical strength is high, the toughness is high, the chemical reaction with the piezoelectric film and the electrode is small, etc.

The respective materials of the protrusion 13, the protective cover 17, and the cap member 19 are not particularly limited, and for example, may be the same as that of the base material 12. The base body 12, the protrusion 13, the protective cover 17, and the cap member 19 may be integrated in such a manner that the respective components are assembled with each other and then sintered after they are molded. Alternatively, the respective structural components or parts of the structural components may adhere to each other by glass, an organic adhesive, or the like.

The piezoelectric film 22 can be suitably made of piezoelectric ceramics, but may be made of electrostrictive ceramics or ferro-electric ceramics. The piezoelectric film 22 may be made of a material required to be subjected to a polarization process or a material not required to be subjected to the polarization process.

The ceramics used for the piezoelectric film may be, for example, ceramics containing lead zirconate, lead magnesium niobic acid, lead nickel niobic acid, lead zinc niobic acid, lead manganin niobic acid, lead antimonic stannic acid, lead titanium acid, lead manganic tungsten acid, lead cobalt niobic acid, barium titanate or the like, or containing the components of any combination of the above material.

Also, the piezoelectric film may be the above ceramics to which oxide of lanthanum, calcium, strontium, molybdenum, tungsten, barium, niobium, zinc, nickel manganin or the like, any combination of the above material, or other compounds are appropriately added. For example, the use of ceramics which mainly contain components consisting of lead magnesium niobic acid, lead zirconate, lead titanium acid in addition to ceramics containing lanthanum or strontium.

It is preferable that the electrode 24a is solid at room temperature and made of conductive metal. For example, there is used metal simple substance or the metal alloy containing aluminum, titanium, chromium, iron, cobalt, nickel, copper, zinc, niobium, molybdenum, lutetium, rhodium, silver, tin, tantalum, tungsten, iridium, platinum, gold, lead, or the like.

It is preferable that the electrode 24b is made of a simple substance or an alloy containing metal having a high melting point such as platinum, lutetium, rhodium, paradium, iridium, titanium, chromium, molybdenum, tantalum, tungsten, nickel, cobalt, or the like. This is because the electrode 24b is exposed at a high temperature while the piezoelectric film is thermally treated, and therefore it is preferably made of metal that withstands a high-temperature oxidation atmosphere. Also, it may be made of cermet containing those high-melting point metal and ceramics such as alumina, zirconium, silicon oxide, or glass.

Subsequently, a description will be given of a method of manufacturing the sensor device body of the present invention.

A base body can be integrated by laminating molded layers of green sheets or green tapes by thermocompression bonding or the like and then sintering the laminated layers. For example, in the base body 12 shown in FIGS. 1A and 1B, three layers of green sheets or green tapes are laminated, and a through-hole of a predetermined shape which will form the space 16 is defined in the second layer in advance before those layers are laminated.

Also, the molded layer is formed by pressure molding using a molding die, cast molding, injection molding, or the like, and then a space or the like may be formed in the molded layer by a mechanical process such as cutting, grinding machining, laser machining, punching due press machining, or the like. The molded layers may not be identical in thickness with each other, but it is preferable that the thickness of the respective layers is set so that contraction due to sintering is the same degree.

As a method of forming the piezoelectric element 20 on the vibrating portion 14, there is a method of molding a piezoelectric body through a press molding method using a mold or a press molding method using a slurry raw material, laminating the piezoelectric body which has not yet been sintered on the vibrating portion of the substrate which has not yet been sintered by thermocompression bonding, and simultaneously sintering it to form the substrate and the piezoelectric body. In this case, it is necessary to previously form the electrode on the substrate or the piezoelectric body through a film forming method which will be described later.

The temperature at which the piezoelectric film is sintered is appropriately determined according to a material that forms the piezoelectric film, but in general, it is 800° to 1400° C., and preferably 1000° to 1400° C. In this case, in order to control the composition of the piezoelectric film, it is preferable that the piezoelectric film is sintered under the condition where an evaporation source of the piezoelectric material exists.

On the other hand, in the film forming method, the electrode 24b, the piezoelectric film 22, and the electrode 24a are laminated on the vibrating portion 14 in the stated order to form the piezoelectric element 20. There is appropriately applied a known film forming method, for example, a thick-film method such as screen printing, a coating method such as dipping, ion beam, sputtering, vapor deposition, ion plating, chemical vapor deposition method (CVD), a thin-film method such as plating, or the like. However, the film forming method of the present invention is not limited to those methods. Among them, the screen printing method is preferable because it allows the film to be stably manufactured.

If the piezoelectric film is formed through the film forming method as described above, the piezoelectric element and the vibrating portion can be integrally bonded to each other without using adhesive, whereby it is excellent in reliability and reproducibility, and further integration is facilitated. As a result, the above method is particularly preferable. Also, the shape of such a film is formed by appropriate pattern. The pattern may be formed by the screen printing method, the photolithography method, or the like. Also, unnecessary parts are removed by using the mechanical machining method such as the laser machining method, slicing or supersonic wave machining to pattern the piezoelectric film.

Then, the respective films (22, 24a, and 24b) formed on the substrate as described above are heat-treated every time each film is formed such that the respective films are integral with the substrate. Alternatively, those films are heat-treated simultaneously after they are formed, so that the respective films are integrally bonded to the substrate. It should be noted that in the case of forming the electrodes through the thin-film method, the heat treatment is not always required in order to integrate those electrodes.

As was described above, according to the present invention, in the space where the fluid to be measured is brought in contact with the vibrating portion, the gas within the space is liable to be replaced by the fluid to be measured, thereby being capable of readily introducing the fluid to be measured within the space.

The foregoing description of a preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A sensor device, comprising:

a base body having a vibrating portion;

a piezoelectric element fixed onto one surface of said vibrating portion and having a piezoelectric film and a pair of electrodes which are in contact with said piezoelectric film;

a space which is defined within said base body and allows a fluid to lead to the other surface of said vibrating portion; and introduction holes that communicate with said space;

wherein said sensor device is in a longitudinal shape, and said space forms a cylindrical space and has a gas exhaust hole that opens on one end portion of said cylindrical space.

2. A sensor device as claimed in claim 1, wherein said space has at least a drawing portion formed on the boundary of a part corresponding to said piezoelectric element.

* * * * *